(12) United States Patent
Joshi et al.

(10) Patent No.: US 11,135,005 B2
(45) Date of Patent: Oct. 5, 2021

(54) FORCEPS HAVING REMOVABLE TIPS

(71) Applicant: MICROLINE SURGICAL, INC., Beverly, MA (US)

(72) Inventors: Sharad H. Joshi, Hopkinton, MA (US); Michael Moniz, Waltham, MA (US); Michael Bentwood, Plymouth, NH (US); Alan Radcliffe, Burlington, MA (US); Shekhar Nimkar, Swampscott, MA (US)

(73) Assignee: Microline Surgical, Inc., Beverly, MA (US)

( * ) Notice: Subject to any disclaimer, the term of this patent is extended or adjusted under 35 U.S.C. 154(b) by 931 days.

(21) Appl. No.: 15/671,665

(22) Filed: Aug. 8, 2017

(65) Prior Publication Data

US 2019/0046258 A1    Feb. 14, 2019

(51) Int. Cl.
*A61B 18/14* (2006.01)
*A61B 18/08* (2006.01)
(Continued)

(52) U.S. Cl.
CPC ........ *A61B 18/1442* (2013.01); *A61B 18/085* (2013.01); *A61B 2017/0046* (2013.01); *A61B 2017/00473* (2013.01); *A61B 2017/00477* (2013.01); *A61B 2017/00526* (2013.01); *A61B 2018/0094* (2013.01); *A61B 2018/00172* (2013.01); *A61B 2018/00595* (2013.01); *A61B 2018/145* (2013.01); *A61B 2018/1462* (2013.01)

(58) Field of Classification Search
CPC .............. A61B 18/085; A61B 18/1442; A61B 2017/0046; A61B 2017/00473; A61B 2017/00477; A61B 2017/00526; A61B 2018/00172; A61B 2018/00595; A61B 2018/0094; A61B 2018/145; A61B 2018/1462

See application file for complete search history.

(56) References Cited

U.S. PATENT DOCUMENTS

| 4,938,214 A | * | 7/1990 | Specht | ................ A61B 17/062 606/167 |
| 5,332,275 A | * | 7/1994 | Conway | .................... B25J 7/00 294/100 |

(Continued)

*Primary Examiner* — Michael F Peffley
*Assistant Examiner* — Amanda L Zink
(74) *Attorney, Agent, or Firm* — Kilpatrick Townsend & Stockton LLP

(57) ABSTRACT

An electronic forceps system includes a handle including a pair of pivotable arms distally extending from a proximal end of the handle, at least one arm of the pair of arms having an electrically-conductive arm element connectable to a power source, wherein each arm of the pair of arms comprises a respective pair of arm interfaces, and the electrically-conductive arm element extends to at least one interface of the pair of interfaces. Also provided is a pair of tips, at least one tip of the pair of tips having an electrically-conductive tip element, wherein each tip has a tip interface configured to removably connect to a respective arm interface, each tip has a distal working surface, the electrically-conductive tip element is configured to removably and electrically connect to the electrically-conductive arm element, the electrically-conductive tip element is connected to a heater.

38 Claims, 12 Drawing Sheets

(51) Int. Cl.
  *A61B 17/00* (2006.01)
  *A61B 18/00* (2006.01)

(56) References Cited

U.S. PATENT DOCUMENTS

| | | | |
|---|---|---|---|
| 5,792,165 A * | 8/1998 | Klieman | A61B 17/29 |
| | | | 606/170 |
| 6,190,386 B1 * | 2/2001 | Rydell | A61B 18/1442 |
| | | | 606/50 |
| 6,235,027 B1 * | 5/2001 | Herzon | A61B 18/085 |
| | | | 606/28 |
| 6,309,397 B1 * | 10/2001 | Julian | A61B 17/00234 |
| | | | 128/898 |
| 6,626,901 B1 | 9/2003 | Treat et al. | |
| 7,011,656 B2 | 3/2006 | McGaffigan et al. | |
| 7,329,255 B2 | 2/2008 | McGaffigan | |
| 9,326,785 B2 | 5/2016 | Joshi et al. | |
| 2003/0158549 A1 * | 8/2003 | Swanson | A61B 18/1482 |
| | | | 606/41 |
| 2004/0193211 A1 * | 9/2004 | Voegele | A61B 5/6838 |
| | | | 606/205 |
| 2009/0125012 A1 * | 5/2009 | Rioux | A61B 18/1445 |
| | | | 606/33 |
| 2013/0046295 A1 * | 2/2013 | Kerr | A61B 18/1445 |
| | | | 606/41 |
| 2014/0314818 A1 * | 10/2014 | Giare-Patel | A61L 29/106 |
| | | | 424/400 |
| 2016/0030240 A1 * | 2/2016 | Gonenc | G01L 25/00 |
| | | | 604/95.01 |
| 2019/0046259 A1 * | 2/2019 | Batchelor | A61B 18/1233 |

* cited by examiner

FORCEPS HAVING REMOVABLE TIPS

BACKGROUND

1. Field of the Disclosure

This invention relates to a laparoscopic instrument assembly having a removable tip, and in particular, a thermal cautery forceps having a pair removable tips.

2. Background of the Disclosure

In the field of disposable medical instruments such as electronically-actuated forceps, it is necessary to balance reducing the cost of each instrument with maintaining quality. If the costs are too great, then sales could be lost, especially given the large number of disposable devices which must be purchased, in comparison to reusable instruments. If quality is sacrificed in the name of saving costs, then there is safety risk to the patient in the event of product failure.

U.S. Pat. No. 7,329,255 discloses a disposable device which can be used to thermally cut, seal or weld tissue. This device includes a complete single assembly including handle, arms and cord, all of which must be disposed of together.

There has thus arisen a need for a device having components which may be separably disposed of or reused, thereby saving costs while still maintaining product quality.

SUMMARY OF THE DISCLOSURE

A feature of the disclosure provides an electronic forceps system including having a handle having a pair of arms distally extending from a proximal end of the handle, the pair of arms configured to pivot towards and away from each other, at least one arm of the pair of arms having an electrically-conductive arm element connectable to a power source, wherein each arm of the pair of arms includes an arm interface, and the electrically-conductive arm element extends to at least one arm interface of the pair of arm interfaces; and a pair of tips, at least one tip of the pair of tips having an electrically-conductive tip element, wherein: each tip of the pair of tips has a tip interface configured to removably connect to a respective arm interface; each tip of the pair of tips has a distal working surface; the electrically-conductive tip element is configured to removably and electrically connect to the electrically-conductive arm element; and the electrically-conductive tip element is connected to a heater on the distal working surface.

The pair of arms further may have a magnetically-actuated switch configured to actuate the heater when the pair of arms moves towards each other, and further configured to deactivate the heater when the pair of arms moves away from each other. The magnetically-actuated switch may be a magnetic reed switch.

Each arm of the pair of arms further may have a frame completely covered by an electrically and fluidically insulative covering which is more flexible than the frame. Each arm of the pair of arms may be jogged along the length of thereof.

Also, each arm of the pair of arms further may have a frame covered by an electrically and fluidically insulative covering which is more flexible than the frame, wherein the pair of arms further may have a magnetically-actuated switch affixed to the frame and configured to actuate the heater when the pair of arms moves towards each other, and further configured to deactivate the heater when the pair of arms moves away from each other.

In another aspect, each tip interface may be configured to removably connect to each respective arm interface by axially inserting one of the tip interface and the arm interface into and along the length of the other of the tip interface and the arm interface, such that each tip is secured to and aligns with a respective arm.

Each tip interface may be configured to removably connect to the arm interface by axially inserting the tip interface into and along the length of the arm interface, each arm interface further may have a movable lock configured to engage the tip interface such that each tip is secured to and aligns with a respective arm.

The movable lock may have a tab end, and a cam end, wherein when the tab end is pushed, the cam end pivots such that a cam surface engages a said tip interface. Also, each arm may have a recess, and upon engagement of the cam surface with the tip interface, the tab end fits in the recess of each respective arm.

Further, each tip interface may be split into two prongs along the length thereof, with a channel between the two prongs, and each arm further may have a pin extending orthogonally to the length direction of the tip interface, such that upon the insertion of the tip interface into the arm interface, the pin slides in the channel. The tip interface may be configured to removably connect to the arm interface via at least one of press-fit connection, bayonet connection, peg-and-hole connection, screw connection, rotator knob connection, movable lock, and cam locking lever connection. Also, the electrically-conductive arm element may be a wire. The electrically-conductive arm element may be unitarily formed with a respective said arm.

The pair of tips may be proximally interconnected such that the pair of tips may have a tweezer configuration.

In another feature of the disclosure, one of each said tip interface and each said arm interface may have a tab, the other of each said tip interface and each said arm interface may have an attachment slot with an opening configured to receive the tab, the tab may be guidable in the attachment slot along the length direction of a respective said arm to attach the respective said tip to a respective said arm.

One of each said tip interface and each said arm interface further may have a guide pin, the other of each said tip interface and each said arm interface further may have a guide slot configured to receive the guide, the guide pin may be guidable in the guide slot along the length direction of a respective said arm.

In another aspect of the disclosure, provided may be forceps handpiece having a handle; a pair of arms distally extending from the handle and configured to pivot towards and away from each other, at least one arm of the pair of arms having an electrically-conductive arm element connectable to a power source, wherein each arm of the pair of arms may have a respective pair of arm interfaces; and the electrically-conductive arm element extends to at least one interface of the pair of arm interfaces; each arm interface of the pair of arm interfaces may be configured to mechanically connect to a respective tip interface of a pair of tips; and at least one arm interface may be configured to electrically connect to a heater on a distal working surface of a respective at least one tip of the pair of tips via the arm element.

The pair of arms further may have a magnetically-actuated switch configured to actuate the heater when the pair of arms moves towards each other, and further configured to deactivate the heater when the pair of arms moves away from each other. The magnetically-actuated switch may be a magnetic reed switch.

Each arm of the pair of arms further may have a frame covered by an electrically and fluidically insulative covering which is more flexible than the frame. Each arm of the pair of arms may be jogged along the length of thereof.

Each arm of the pair of arms further may have a frame covered by an electrically and fluidically insulative covering which is more flexible than the frame, wherein the pair of arms further may have a magnetically-actuated switch affixed to the frame and configured to actuate the heater when the pair of arms moves towards each other, and further configured to deactivate the heater when the pair of arms moves away from each other. The arm interface may be configured to removably connect to the tip interface by axially inserting one of the tip interface and the arm interface into and along the length of the other of the tip interface and the arm interface, such that each tip is secured to and aligns with a respective arm. The arm interface may also be configured to removably connect to the tip interface via one of press-fit connection, bayonet connection, peg-and-hole connection, screw connection, rotator knob connection, movable lock, and cam locking lever connection.

Another aspect of the disclosure provides forceps tip system having a pair of tips; a pair of tip interfaces respectively located at a proximal end of the pair of tips, the pair of tip interfaces configured to removably connect to a respective pair of arm interfaces of a respective pair of arms of a forceps handle; a pair of working surfaces located on respective distal ends of the pair of tips; an electrically-conductive tip element located on at least one tip of the pair of tips and configured to electrically connect to a respective at least one arm interface of the pair of arm interfaces; and a heater located on the at least one working surface of the pair of working surfaces and electrically connected to the electrically-conductive tip element.

The pair of tip interfaces may be configured to removably connect to the respective pair of arm interfaces by axially inserting one of the pair of tip interfaces and the pair arm interfaces into and along the length of the other of the pair of tip interfaces and the pair of arm interfaces, such that the pair of tips is respectively secured to and aligns with the pair of arms.

The pair of tip interfaces may be configured to removably connect to the pair arm interfaces via one press-fit connection, bayonet connection, peg-and-hole connection, screw connection, rotator knob connection, movable lock, and cam locking lever connection.

The tip system may further have another electrically-conductive tip element located on a second tip of the pair of tips and configured to electrically connect to a respective second arm interface of the pair of arm interfaces; and another heater located on a second working surface of the pair of working surfaces and electrically connected to the another electrically-conductive tip element.

A further aspect of the disclosure provides a forceps tip alignment system having an upper half having a pair of upper channels, and a lower half having a pair of lower channels, wherein the pair of upper and lower channels together are configured to removably accommodate and maintain in alignment a respective pair of forceps tips such that the pair of forceps tips are sandwiched between the upper half and the lower half.

The forceps tip alignment may further have a plurality of pins on one of the upper half and the lower half; and a plurality of sockets on the other of the upper half and the lower half, wherein the plurality of sockets are configured to removably accommodate a respective pin of the plurality of pins such that the upper half and lower half are aligned with each other.

Also provided may be a method of installing and aligning a pair of forceps tips with a respective pair of handpiece arms, each tip of the pair of tips having a tip interface, and each arm of the pair of arms having an arm interface, the method including holding the pair of forceps tips in alignment with each other between two halves of an alignment tool, inserting each tip interface into a respective arm interface such that the pair of forceps tips is attached to a respective pair of arms, and removing the two halves of the alignment tool from the pair of forceps tips. The method may further include, before removing the two halves of the alignment tool from the pair of forceps tips, pivoting a lock on each arm to secure a respective said tip to a respective said arm.

Yet another aspect of the disclosure provides an electronic forceps kit having a handle having a pair of arms distally extending from a proximal end of the handle, the pair of arms configured to pivot towards and away from each other, at least one arm of the pair of arms having an electrically-conductive arm element connectable to a power source, wherein each arm of the pair of arms includes an arm interface, and the electrically-conductive arm element extends to at least one arm interface of the pair of arm interfaces, and a pair of tips, at least one tip of the pair of tips having an electrically-conductive tip element, wherein each tip of the pair of tips may have a tip interface configured to removably connect to a respective arm interface, each tip of the pair of tips may have a distal working surface, the electrically-conductive tip element may be configured to removably and electrically connect to the electrically-conductive arm element, and the electrically-conductive tip element is connected to a heater on the distal working surface, and a forceps tip aligner having: an upper half having a pair of upper channels; and a lower half having a pair of lower channels, wherein the pair of upper and lower channels together are configured to removably accommodate and maintain in alignment a respective tip of the pair of forceps tips such that the pair of forceps tips are removably sandwiched between the upper half and the lower half.

Other exemplary embodiments and advantages of the present invention may be ascertained by reviewing the present disclosure and the accompanying drawings, and the above description should not be considered to limit the scope of the present invention.

BRIEF DESCRIPTION OF THE DRAWINGS

The present invention is further described in the detailed description which follows, in reference to the noted plurality of drawings, by way of non-limiting examples of preferred embodiments of the present invention, in which like characters represent like elements throughout the several views of the drawings, and wherein.

DETAILED DESCRIPTION

Figure 1:
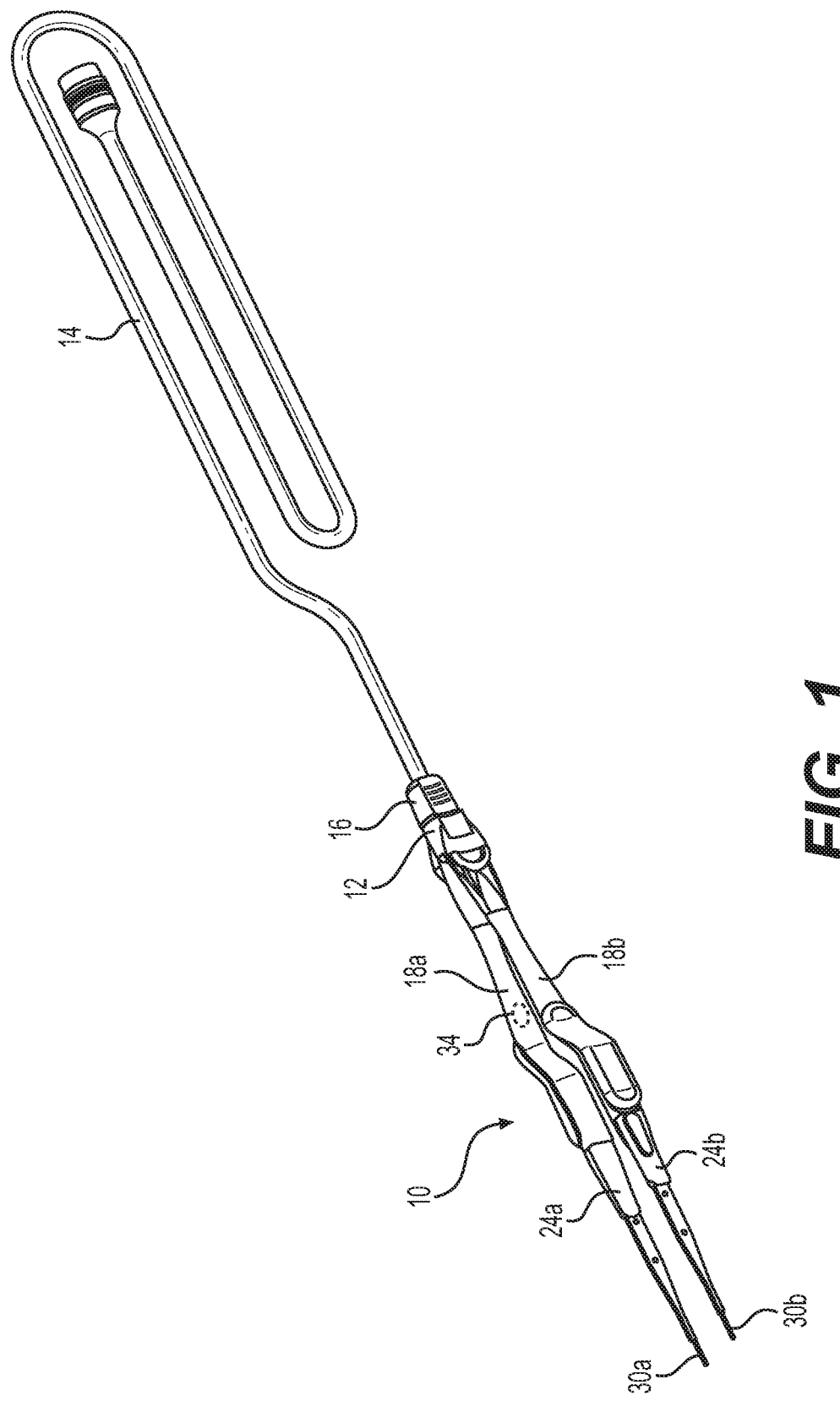
FIG. 1 shows a perspective view of an assembled forceps system, in accordance with a feature of a first embodiment of the present disclosure.

The particulars shown herein are by way of example and for purposes of illustrative discussion of the embodiments of the present invention only, and are presented for providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Referring to the drawings wherein like characters represent like elements, FIGS. 1-4 show a forceps system 10 in accordance with the disclosure. In an aspect, the forceps system is a thermal cautery forceps system; however, it is appreciated that the disclosure may employ other types of forceps systems in other aspects, such as an electro-surgical forceps system.

The system 10 includes a handle 12 connectable to a power source via a power cord 14. The power cord 14 is removably connectable to a proximal end of the handle 12 via a plug 16. The handle 12 includes a pair of arms 18a, 18b distally extending from the proximal end of the handle at a hinge 13, which allows the pair of arms 18a, 18b to pivot toward and away from each other in the manner of a forceps or tweezer. The hinge has a geometry which allows for reduced user hand fatigue as well as the durability required to retain its integrity after numerous cleaning and sterilization cycles of the handle 12. Further, the hinge geometry also prevents torqueing of the handle, which would otherwise cause tip misalignment. Additionally, in accordance with a feature of the disclosure, each arm 18a, 18b has a jogged "Z" shape, which keeps the hinge 13 and power cord 14 out of the user's way during use.

Figure 3:
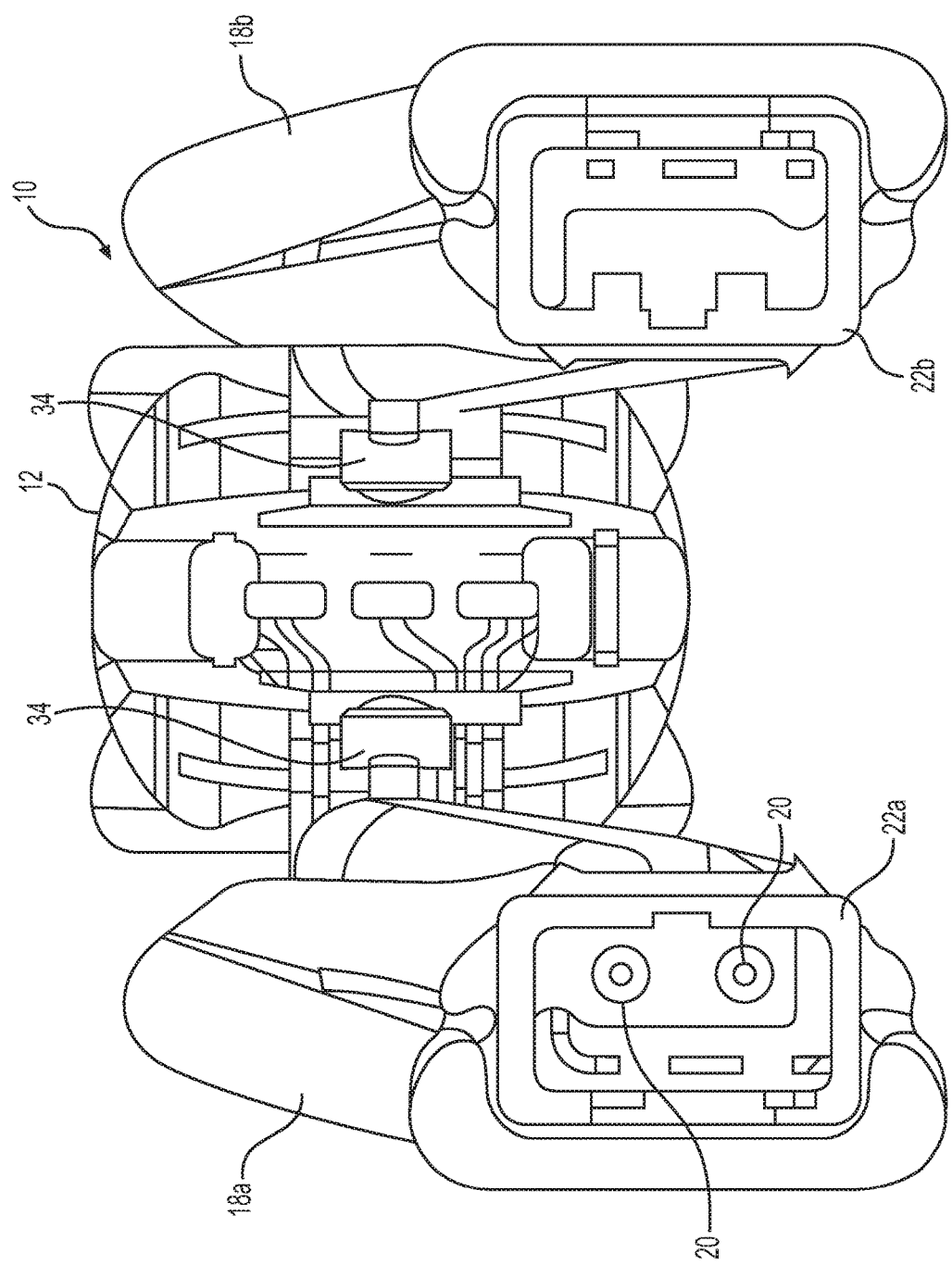
FIG. 3 shows a front view of the handle of the forceps system in accordance with a feature of the first embodiment of the present disclosure.
Figure 4:
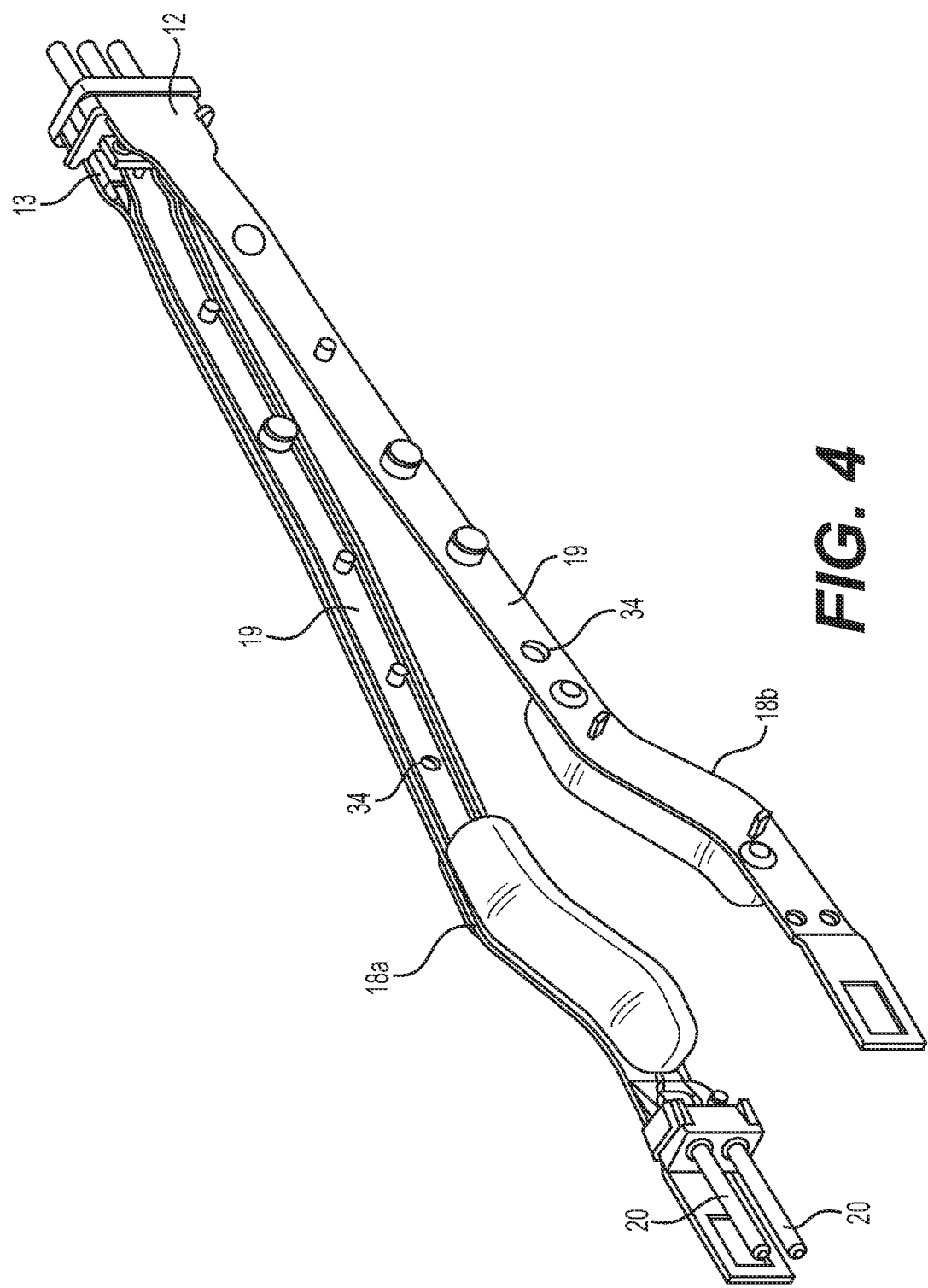
FIG. 4 shows a perspective view of the handle of the forceps system without a sheath, in accordance with a feature of the first embodiment of the present disclosure.

At least one electrically-conductive wire 20 extends along the length of the handle 12, through at least one arm 18a, 18b, where a proximal end of the wire at the proximal end of the handle can connect with the plug 16, and where a distal end of the wire is located at an arm interface 22a, 22b. Although FIGS. 3-4 show two wires 20 (arm wires or arm elements) at only arm interface 22a, it is noted that fewer or greater than two wires may be employed in a single one of or in both arm interfaces 22a, 22b, depending on the desired application (e.g., should a sensor be employed in one or both arm interfaces 22a, 22b to detect the presence or absence of tips 24a, 24b). It is further noted that that the arm elements 20 may be unitarily formed with a respective arm 18a, 18b (i.e. formed of a single piece of material with the arm).

Figure 2:
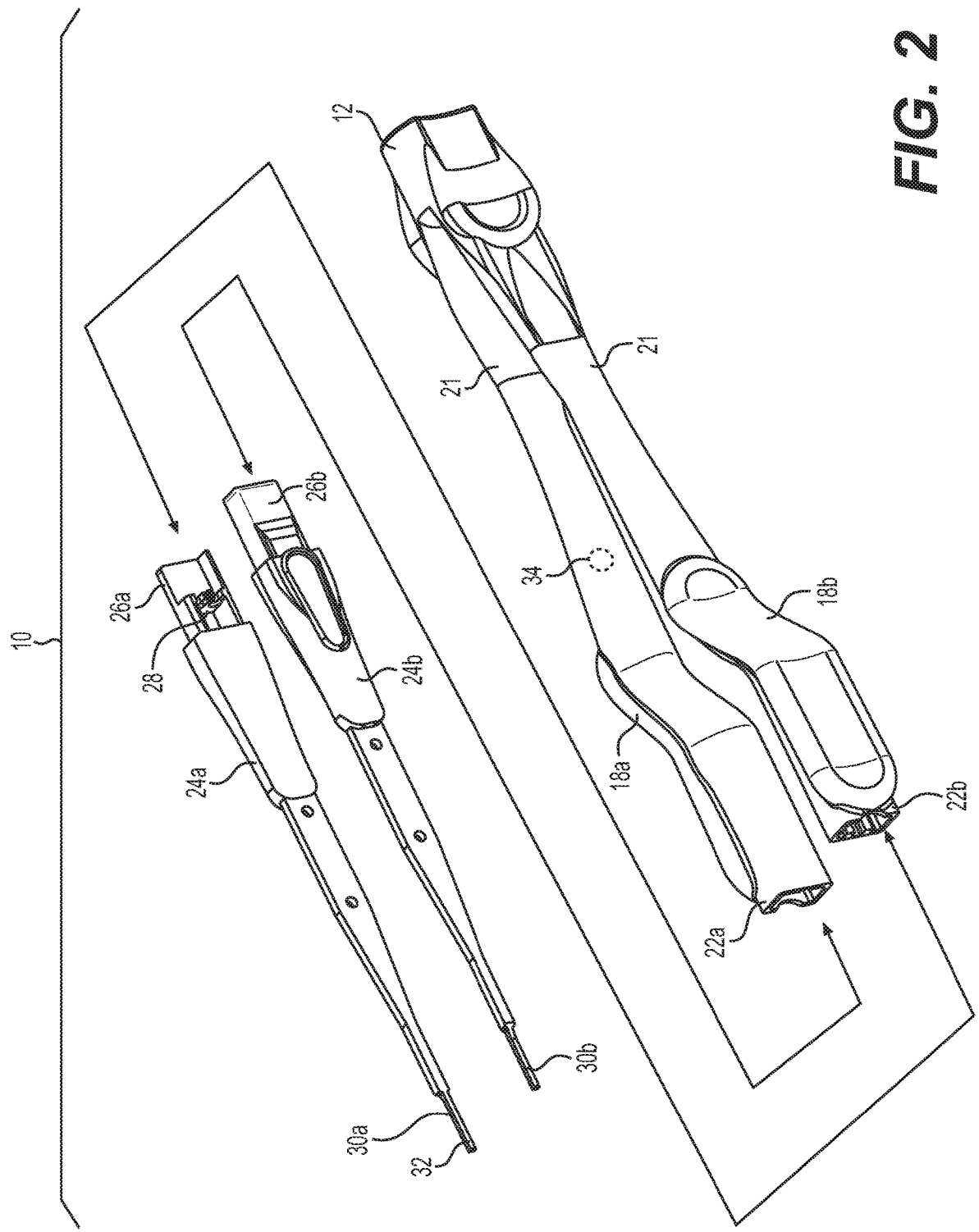
FIG. 2 shows a perspective view of the forceps system prior to assembly, in accordance with a feature of the first embodiment of the present disclosure.

In an aspect of the disclosure and as shown in FIG. 4, each arm 18a, 18b includes a metal frame 19 overmolded with an electrically-impermeable and fluid-impermeable plastic sheath 21 (shown in FIG. 2). The frame 19 provides support for the plastic sheath 21 during the overmolding process, as well as support for any electronic and other components installed on the frame. In conjunction with the durometer of the sheath 21, the frame allows the arms 18a, 18b to be "tuned" during the manufacturing process for the desired compression and/or dissecting forces of the device 10. In accordance with a feature of the disclosure, the durometer of the sheath 21 is in the 90+ Shore A or D scale, making it extremely durable and hard (but more flexible than the frame 19), with limited pliability, although it is noted that material (s) having different durometers may be used, depending on the desired application. The frame 19 also provides anti-torqueing rigidity, which maintains the tip alignment of the device 10.

Referring to FIGS. 1-2, the system 10 also includes a pair of tips (tip arms) 24a, 24b, each tip of the pair of tips having a respective tip interface 26a, 26b respectively connectable to the arm interfaces 22a, 22b on the handle 12. In this way, the pair of tips 24a, 24b can be removably connected to the handle 12. Each tip 24a, 24b has a respective working surface 30a, 30b at a distal end thereof and configured to engage tissue for manipulation, by e.g., thermally cutting, sealing or welding tissue. The tip interface 26a, 26b of the tips 24a, 24b are respectively connectable to the arm interfaces 22a, 22b on the handle 12 by a connection such as a press-fit connection, which allows for the device 10 to be easily assembled by the user.

It is further noted that the press fit connection uniquely holds the tips in axial alignment with the handle, thereby allowing for precise cutting and dissecting during surgery and avoiding injury to the patient due to tip misalignment. It is noted that as an alternative to a press-fit arrangement of the tip interface 26a, 26b into a socket-type arm interface 22a, 22b, the tip interface 26a, 26b of the tips 24a, 24b may be respectively connectable to the arm interfaces 22a, 22b on the handle 12 by other arrangements, including but not limited to thumbscrew, rotator knob or cam locking lever, and that one tip may be connected to the handle by one arrangement, while the other tip may be connected to the handle by another arrangement.

It is noted that the removable connection of the tips 24a, 24b to the handle 12 allows for user to use multiple tip configurations without using numerous devices in one surgery, thereby increasing efficiency during a procedure (e.g., since the basic feel and ergonomics of the same handle is maintained, as a single handle can be used throughout a single procedure), as well as saving costs (since an entire device does not need to be replaced). For example during one phase of a procedure, the user may use serrated tips attached to the handle 12, and during a later phase of the procedure, the user may detach the serrated tips and replace them with smooth tips. It is further noted that removable connection of the tips 24a, 24b to the handle 12 reduces the cost per procedure due to the inexpensive cost of the tips (relative to the cost of an entire device) which can be single-use devices, as well as due to the reusability of the handle (which can be sterilized and reused), which allows for the cost of the handle to be amortized over its life cycle. In other aspects, the tips 24a, 24b can also be separately sterilized and reused.

At least one of the tip 24a, 24b has an electrically-conductive wire 28 (tip wire or tip element) extending along the length of the tip 24a, 24b, where a proximal end of the wire 28 can operably connect to the wire 20 in the handle 12 when the tip interfaces 26a, 26b connect to the arm interfaces 22a, 22b, and where a distal end of the wire 28 extends to a heater 32 (in the form of, e.g., an ohmic resistive heater) on at least one of the working surface 30a, 30b. In this way, the working surfaces 30a, 30b can be electrically actuated by, e.g., providing resistive heating to the wire 28 and/or heater 32 to manipulate tissue when the tips 24a, 24b are connected to the handle 12. It is noted that the system 10 may provide the heater 32 as discrete from the wire 28, or the wire itself may serve as the heater, depending in the desired application.

Although the figures shows two wires 28 at only tip interface 26a, it is noted that fewer or greater than two wires may be employed in a single one of or in both tip interfaces 26a, 26b, depending on the desired application. Further, although the figures show heater 32 on only a single tip working surface 30a (the "active tip") and no heater on the other tip working surface 30b (the "passive tip"), it is noted that a heater (having one or more wires) may be provided on a single working surface or on both working surfaces 30a, 30b, depending on the desired application.

The system 10 also includes a switch 34 on the frame 19 which closes a circuit connected to the power source in order to provide electrical power to heat the heater, such that the user can perform a medical procedure such as thermally cutting, sealing or welding tissue. In accordance with a feature of the disclosure, the switch 34 is a magnetically-actuated switch, and more specifically may be a magnetically-actuated reed switch, although it is understood that other types of switches may be used, depending on the desired application.

In this feature, the switch 34 includes a pair of contacts on ferromagnetic metal reeds, each reed being located on a respective arm 18a, 18b. When the arms 18a, 18b (and therefore the contacts of the switch) approach each other when moved from an open arm position towards a closed arm position (by applying pressure by the user to the arms), a magnetic field is created, which is detected by a computer processor connected to the system 10, which in turn controls the power source to provide power to the system. When the user releases pressure to the arms 18a, 18b, the arms 18a, 18b (and therefore the contacts of the switch 34) move away from each other, interrupting the magnetic field and turning off electrical power to the system 10.

The switch 34 may be actuated by a coil, a reed relay, or by bringing a magnet near the switch (i.e., one of the two contacts may be a magnet). Although the magnetically-actuated reed switch 34 may appear similar to the user in functionality to the related art dome, or membrane, switch, which requires the user to press both arms together so that a protrusion on one arm physically contacts and pushes the dome switch on the other arm to actuate the related-art device, it is noted that in the magnetically-actuated reed switch 34 of the present disclosure, no physical contact between the sensors needs to occur, only that they are proximate each other to create the magnetic field. Therefore, the switch 34 can reduce user hand fatigue, since the user does not have to bring the arms 18a, 18b into contact with each other to actuate the heater 32.

The reed switch 34 may also be fully-encased by the overmolded sheath 21 with no effect on the actuation of the device 10, thereby rendering the switch impervious to the harsh environments of automatic washing and autoclaving the handle 12 for re-use. The reed switch 34 also allows the device 10 to optionally be completely hand activated, whereby the user does not have to locate or be aware of switch (such as a foot switch) located away from the device, thereby allowing the user to give his/her full attention to the unique and precise surgical work performed using the device.

Figure 5:
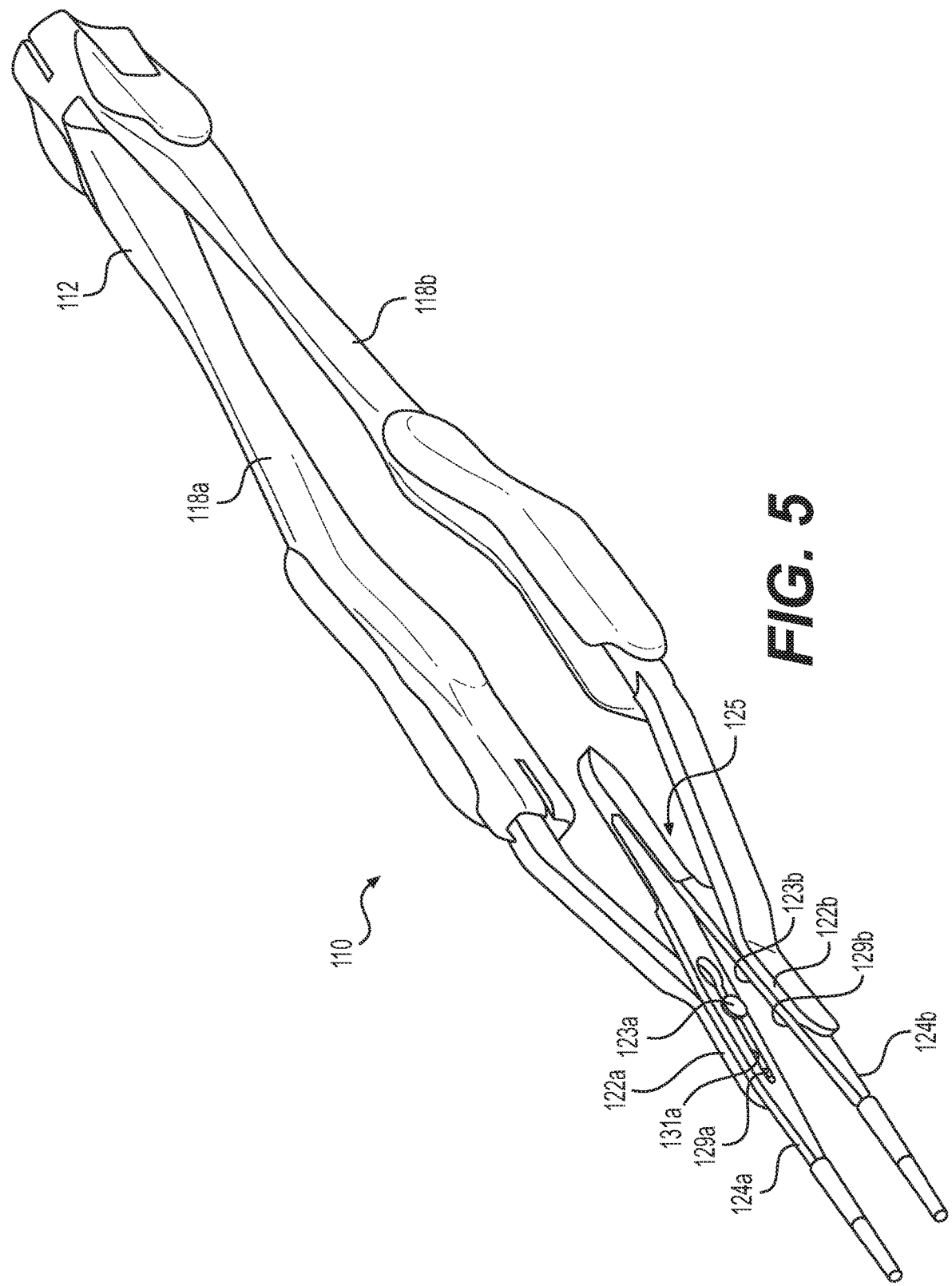
FIG. 5 shows a perspective view of an assembled forceps system, in accordance with a feature of a second embodiment of the present disclosure.
Figure 6:
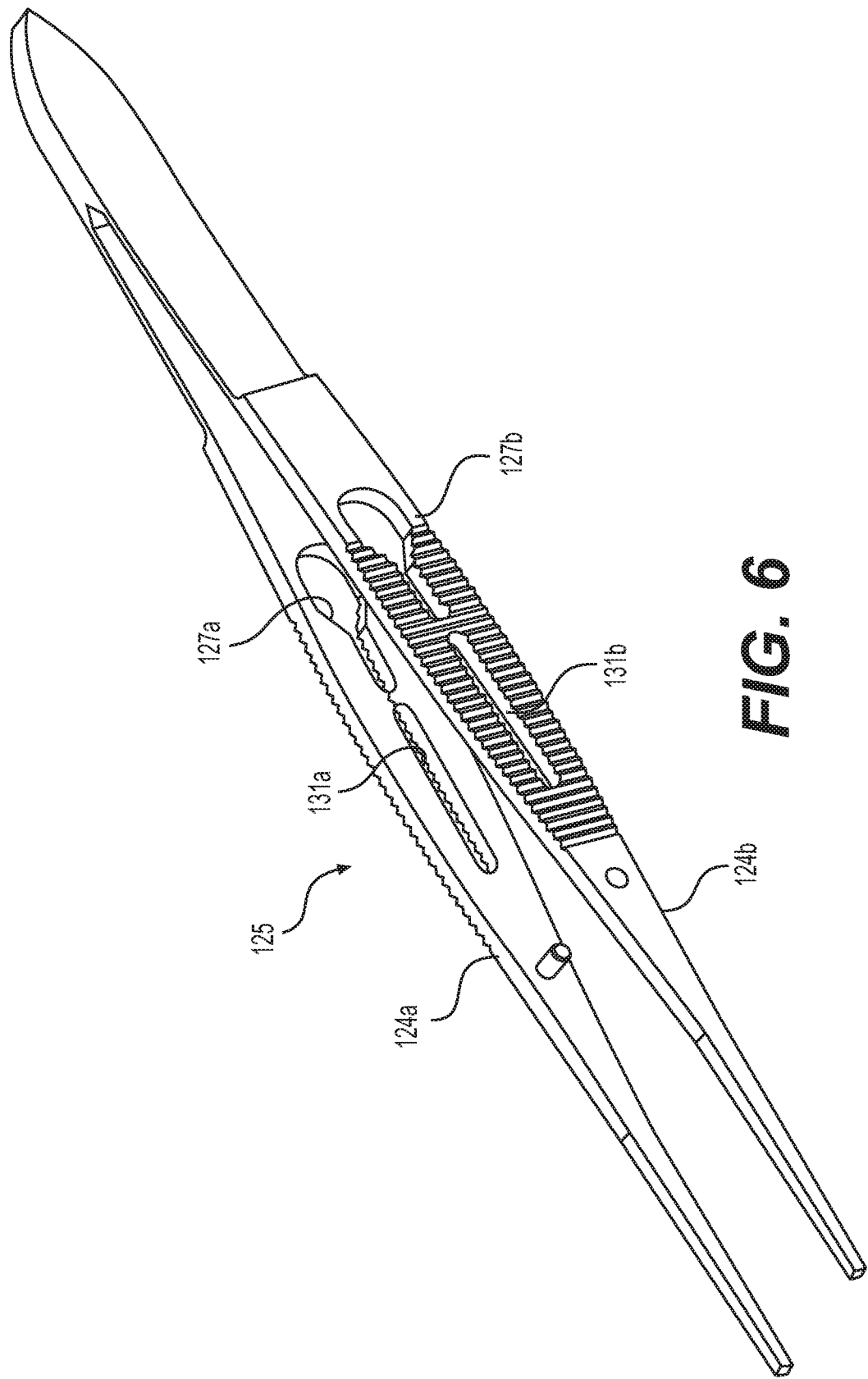
FIG. 6 shows a perspective view of a tip in accordance with a feature of the second embodiment of the present disclosure.

FIGS. 5-6 show a second embodiment of a forceps system 110 in accordance with the disclosure. Unlike the forceps system 10 of the first embodiment (which employs individual tips 24a, 24b), the system 110 of the second embodiment employs a tip 125 having tweezer configuration. For example, the tip 125 includes tip arms 124a, 124b proximally joined together to form a single tweezer-like "V" configuration, which allows the tip arms to move towards and away from each other, as with a tweezer. Since the tip arms 124a, 124b are joined together in a tweezer-like "V" configuration, the tip arms are always maintained in alignment with each other due to the increased lateral stability, thereby reducing harm to the patient due to tip misalignment.

Also unlike the forceps system 10 of the first embodiment (which employs a press-fit arrangement of the tip interface 26a, 26b into a socket-type arm interface 22a, 22b), the system 110 of the second embodiment employs arm interfaces 122a, 122b each having an attachment tab 123a, 123b with an enlarged head and configured to fit into a respective attachment slot 127a, 127b of a respective tip arm 124a, 124b. The attachment slot 127a, 127b has an enlarged opening (i.e., an opening having a larger width than that of the remainder of the slot) at a proximal end thereof to accommodate the enlarged head of the attachment tab 123a, 123b, such that when the attachment tab slides in a proximal direction in the attachment slot 127a, 127b, the attachment tab is captured in the attachment slot. It is also noted that in FIGS. 5-6, the arm elements are unitarily formed with a respective arm 118a, 118b (i.e. formed of a single piece of material with the arm), however it is appreciated that in alternative embodiments a wire similar to that of the first embodiment may be used, depending on the desired application. Although FIGS. 5-6 show the attachment tabs 123a, 123b located on the arm interfaces 122a, 122b, as well as the attachment slots 127a, 127b located on the tip 125, although it is understood that in alternative aspects the attachment tabs 123a, 123b may be on the tip, and the attachment slots 127a, 127b may be on the arm interfaces 122a, 122b, depending on the desired application. 10581 In order to maintain pitch of the tip 125 relative to the arms 118a, 118b (i.e., to avoid unwanted tilting of the tip relative to the arms), the arm interfaces 122a, 122b each have a guide pin 129a, 129b configured to fit into a respective guide slot 131a, 131b of a respective tip arm 124a, 124b. When a guide pin 129a, 129b is inserted in a respective guide slot 131a, 131b, it is slidable therein at the same time the attachment tab 123a, 123b slides in the attachment slot 127a, 127b. Although FIGS. 5-6 show the attachment pins 129a, 129b located on the arm interfaces 122a, 122b, as well as the guide slots 131a, 131b located on the tip 125, it is understood that in alternative aspects the attachment pins 129a, 129b may be on the tip, and the guide slots 131a, 131b may be on the arm interfaces 122a, 122b, depending on the desired application. It is further noted that although FIG. 6 shows guide slots 131a, 131b and attachment slots 127a, 127b as open, either of them can be closed, depending on the desired application.

A method of attaching the tip 125 of the second embodiment to the arm interfaces 122a, 122b of the arms 118a, 118b is now described. Initially, either the arms 118a, 118b of the handle 112 are pulled apart or the tip arms 124a, 124b are squeezed inwardly to provide clearance for and allow the enlarged heads of the attachment tabs 123a, 123b to enter a respective enlarged opening of attachment slot 127a, 127b and at the same time allow the guide pins 129a, 129b to enter a respective guide slot 131a, 131b. Thereafter, the handle is slid proximally (and/or the tip 125 is slid distally) so that the attachment tabs 123a, 123b are in the proximalmost position in a respective attachment slot 127a, 127b, and so that the guide pins 129a, 129b are in the proximalmost position in a respective a guide slot 131a, 131b, thereby securely affixing the tip 125 to the handle 112. The tip 125 may be removed from the handle 112 by performing the above steps in reverse. Once removed, the tip 125 (as well as the handle 112) may be disposed of or sterilized for future use.

FIGS. 7-12 show a third embodiment of a forceps system 210 in accordance with the disclosure. Unlike the forceps systems 10, 110 of the first and second embodiments, the system 210 of the second embodiment employs movable locks to secure the tip arms 224a, 224b to the handle 212, as further described below. In this system 210, optionally provided is a tip alignment device (tip aligner) 250 for maintaining the tip arms 224a, 224b in alignment with each other before and after attachment thereof to the handle 212.

The tip alignment device 250 includes an upper half 254 and a lower half 256 each having channels 258a, 258b configured to removably and securely house a respective tip arm 224a, 224b therein such that the tip arms are immovably held in alignment with each other. In an aspect of the disclosure, the alignment device 250 may be assembled by the manufacturer with the tip arms 224a, 224b assembled therein, whereafter it is provided to a user as a tip alignment device assembly or kit.

Figure 11:
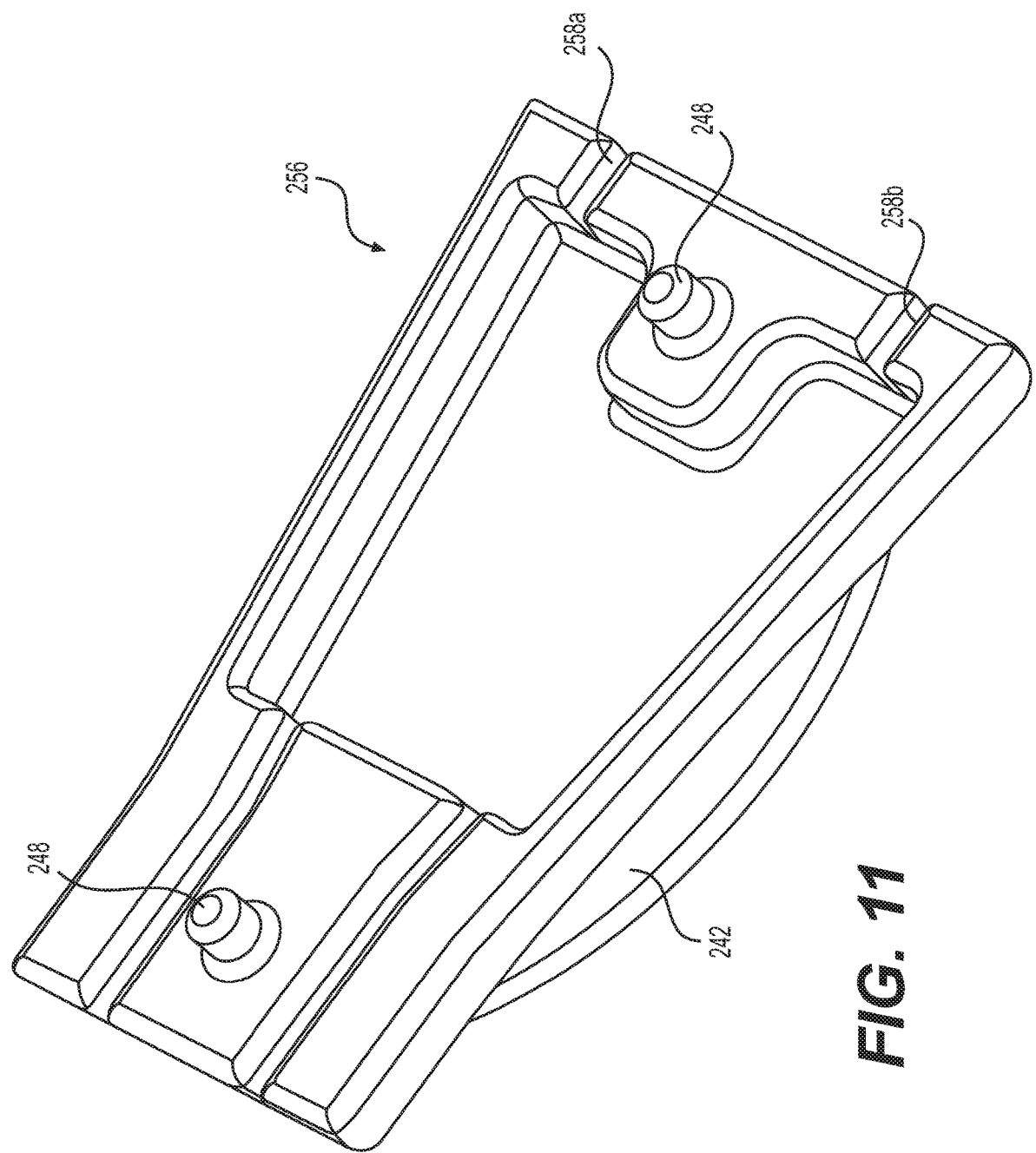
FIG. 11 shows a perspective view of a lower half of an disassembled assembly device for a forceps system in accordance with the feature of a third embodiment of the present disclosure.
Figure 12:
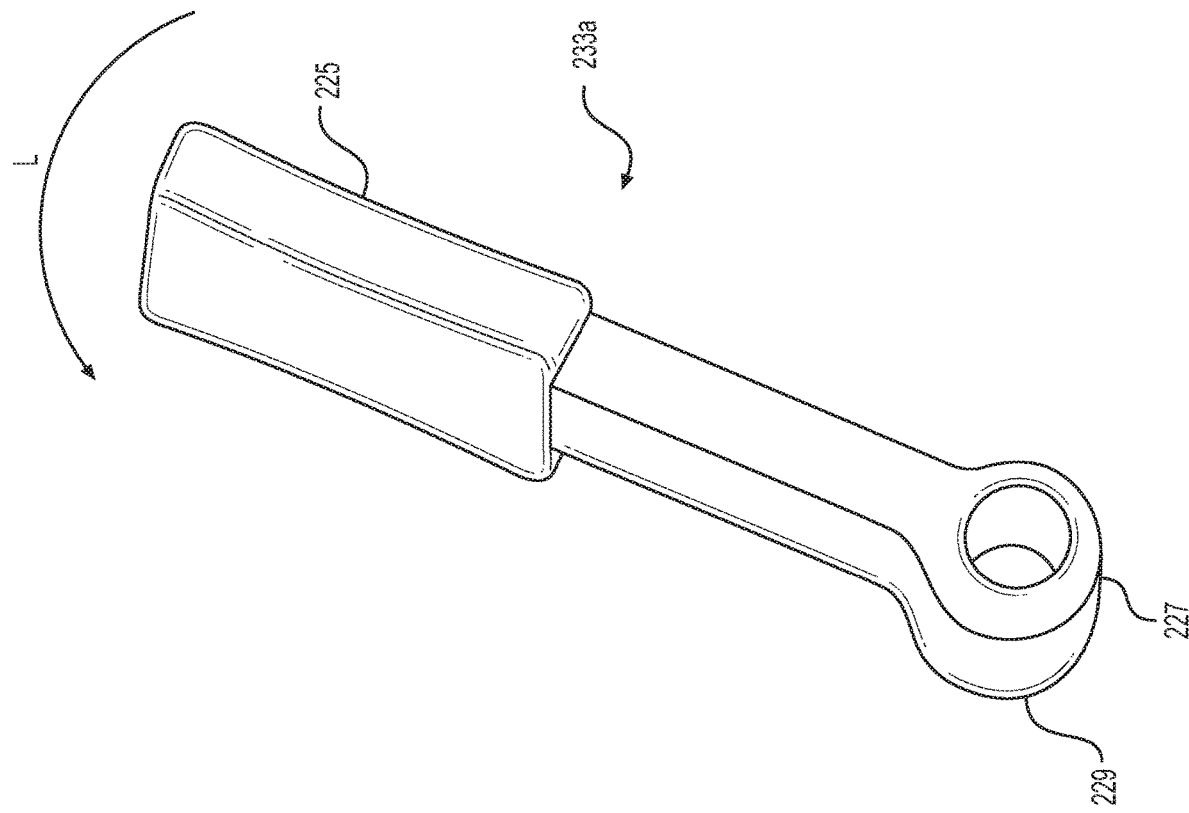
FIG. 12 shows a perspective view of a movable lock of a forceps system in accordance with the feature of a third embodiment of the present disclosure.

As shown in FIG. 11, in order to prevent sliding movement of the upper half 254 and lower half 256, one of them may include a plurality of pins 248 and the other of them may include a complimentary a plurality of sockets 249 configured to removably accommodate a respective pin such that the upper half and lower half are aligned with each other. Although FIG. 11 shows the pins 248 on the lower half 256, it is appreciated that the pins can be positioned on the upper half and the sockets 249 can be positioned on the lower half. Each half 254, 256 of the tip alignment device 250 may include one or more grips 242 to assist in separating the halves once the tip arms 224a, 224b have been affixed to the arms 218a, 218b.

The tip arms 224a, 224b each have a respective tip interface 226a, 226b respectively connectable to the arm interfaces 222a, 222b on the handle 212. In this way, the pair of tip arms 224a, 224b can be removably connected to the handle 212. The tip interface 226a, 226b of the tip arm 224a, 224b are respectively insertable in the arm interfaces 222a, 222b on the handle 212, which allows for the device 210 to be easily assembled by the user.

Each tip interface 226a, 226b may be split into two prongs 226a1, 226a2, 226b1, 226b2 such that a channel 226a3, 226b3 is present therebetween. Each arm interface 222a, 222b may include a pin 261a, 261b extending orthogonally to the length direction of the tip interface 226a, 226b, such that upon the insertion of the tip interface into the arm interface, each pin slides in a respective channel, to improve stability of the tip arms 224a, 224b once they are affixed to the handle 212, thereby reducing harm to the patient due to tip misalignment.

Each arm interface 222a, 222b may include a movable lock 233a, 233b configured to engage a respective tip interface 226a, 226b such that each pre-aligned tip 224a, 224b in the tip alignment device 250 is immovably secured to and aligns with a respective arm 218a, 218b. In particular, each movable lock 233a, 233b includes a tab end 225 and a cam end 227 having a cam surface 229 thereon, wherein when the tab end is pushed in direction L (shown in FIGS. 10 and 12), the cam end 227 pivots about a shaft such that the cam surface 229 presses against a respective tip interface 226a, 226b and immovably secures the tips 224a, 224b to a respective arm 218a, 218b in an alignment relationship. It is noted that the cam surface 229 can directly or indirectly contact a tip interface 226a, 226b, depending on the desired application.

In order to prevent accidental disengagement of the cam surface 229 from the tip interface 226a, 226b, each arm interface 222a, 222b may include a recess 244a, 244b on a surface thereof, whereupon engagement of the cam surface with the tip interface, the tab end 225 fits in the recess of each respective arm. In an aspect of the disclosure, the tab end 225 may fit flush with the surface of a respective arm 218a, 218b.

Figure 7:
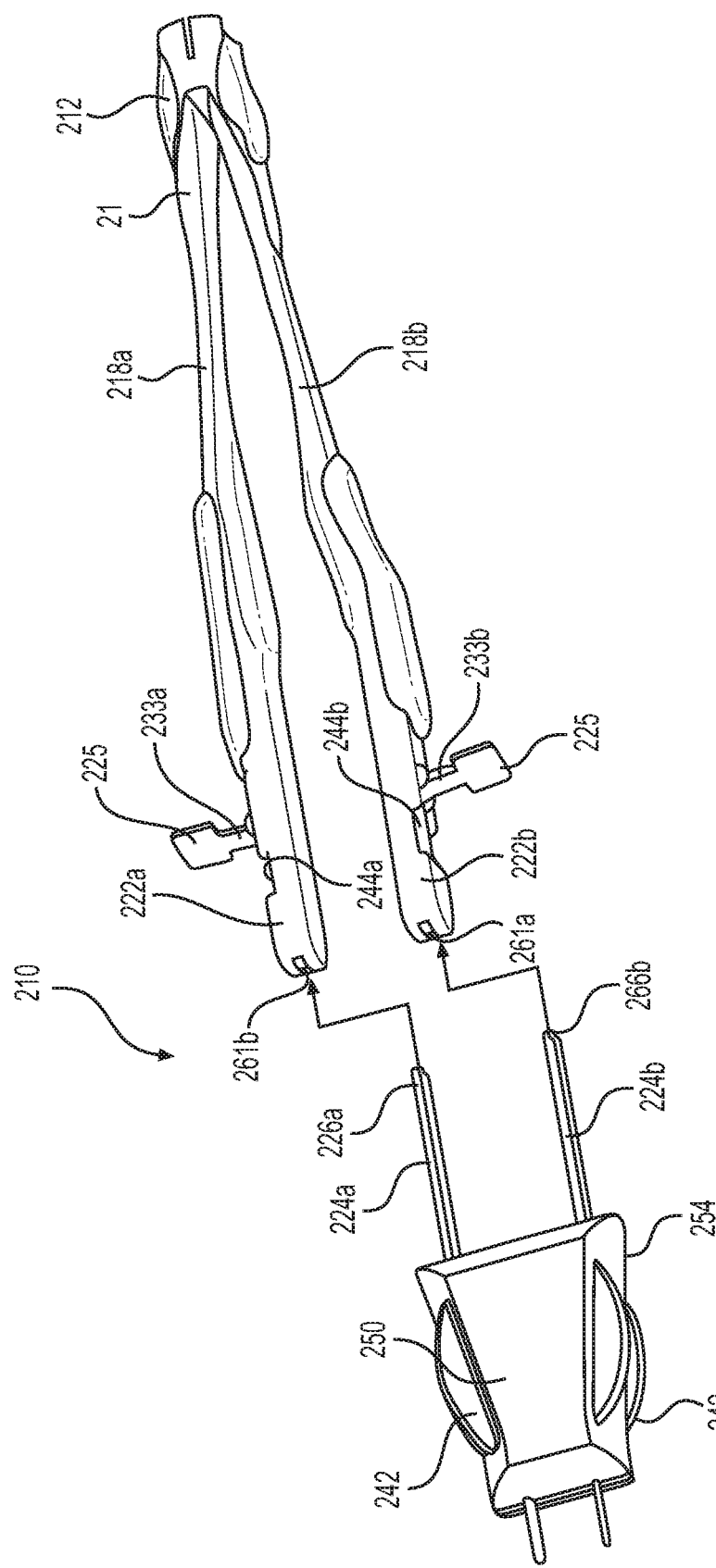
FIG. 7 shows a perspective view of a disassembled forceps system in accordance with a feature of a third embodiment of the present disclosure.
Figure 8:
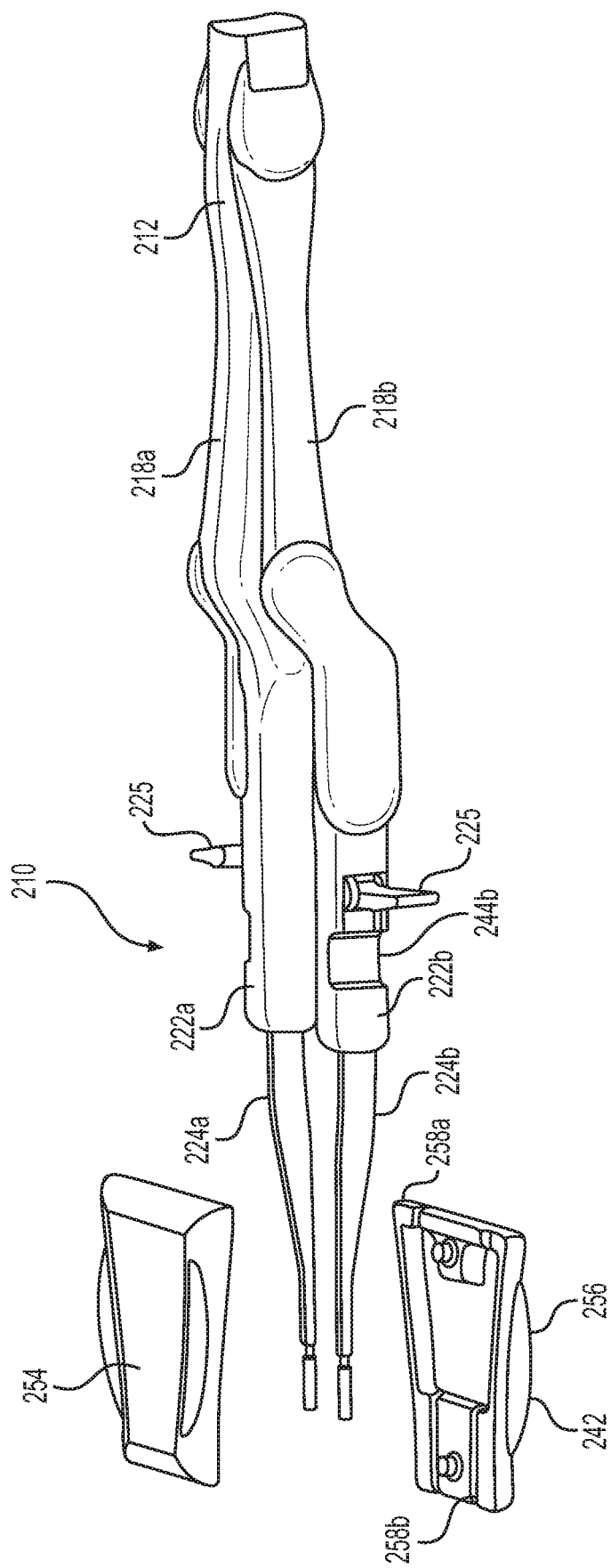
FIG. 8 shows a perspective view of an assembled forceps system and disassembled assembly device in accordance with the feature of a third embodiment of the present disclosure.
Figure 9:
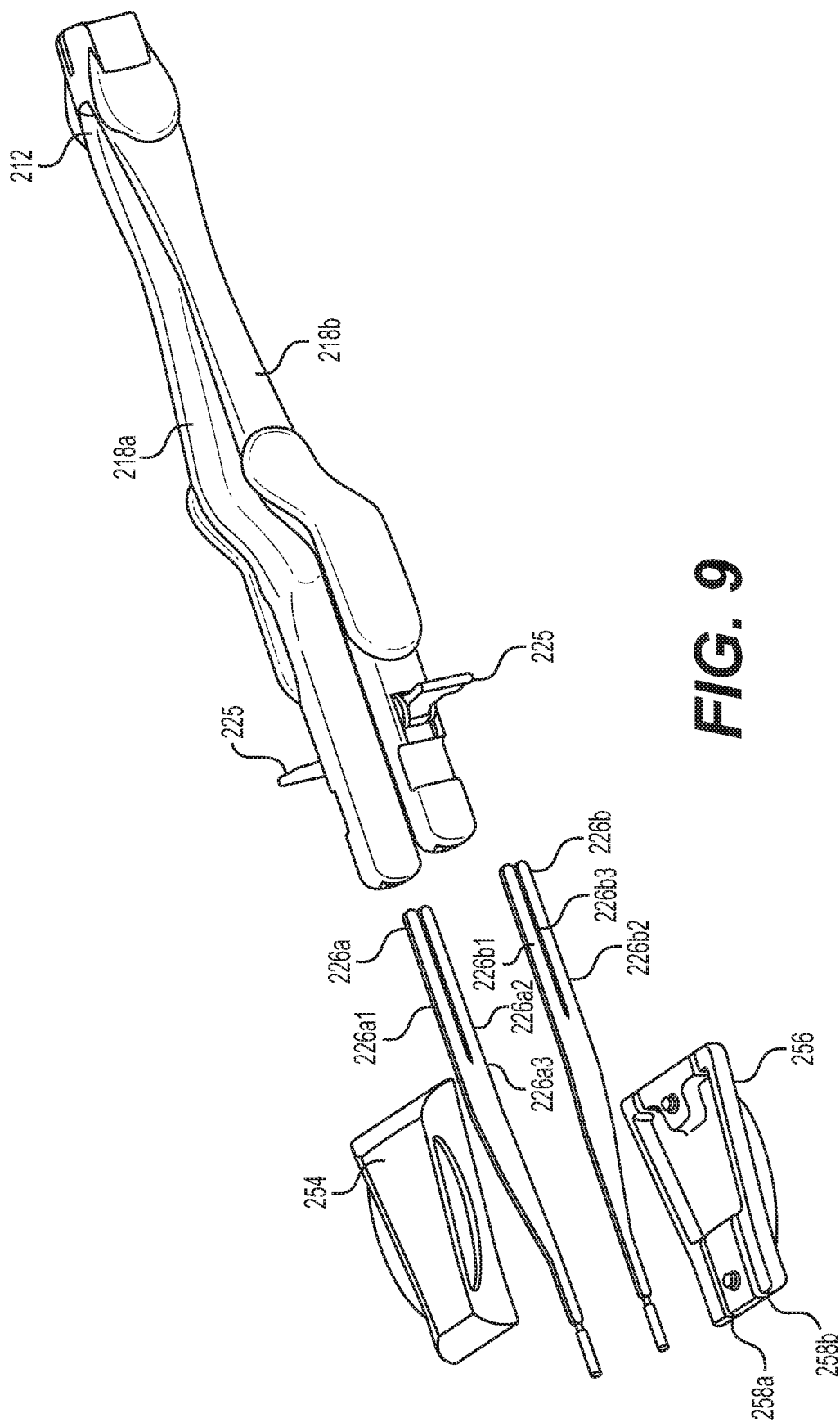
FIG. 9 shows an exploded view of a disassembled forceps system in accordance with the feature of a third embodiment of the present disclosure.
Figure 10:
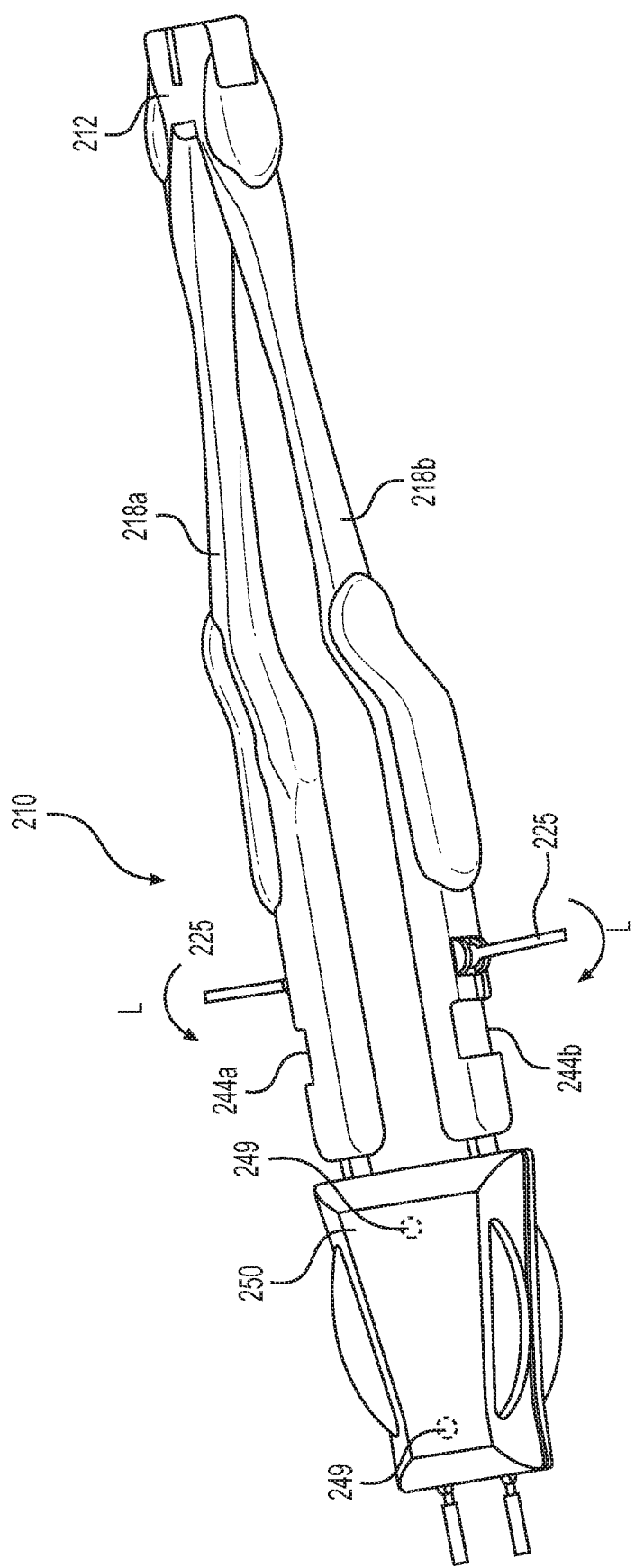
FIG. 10 shows a perspective view of an assembled forceps system and assembly device in accordance with the feature of a third embodiment of the present disclosure.

A method of attaching the tips 224a, 224b of the third embodiment to the arm interfaces 222a, 222b of the arms 218a, 218b is now described. Initially, the user obtains the tip alignment device assembly including the tips 224a, 224b pre-installed and pre-aligned in the tip alignment device 250 (which may arrive in sterile condition). As shown in FIGS. 7 and 10, holding the tip alignment device 250, user then inserts each tip interface 226a, 226b into a respective arm interface 222a, 222b such that the pair of forceps tips 224a, 224b is attached to a respective pair of arms 218a, 218b. The user next pushes the tab end 225 in direction L until it fits into a respective recess 244a, 244b (shown in FIGS. 10 and 12), wherein the cam end 227 pivots about a shaft such that the cam surface 229 firmly presses against a respective tip interface 226a, 226b and immovably secures the tips 224a, 224b to a respective arm 218a, 218b in an alignment relationship. Once the tips 224a, 224b are secured to a respective arm 218a, 218b, the user can then separate the halves 254, 245 of the alignment device 250 to remove it from the pair of tips (where the alignment device may be discarded, recycled or reused), thereby assembling the device, which is now ready for use, as shown in FIG. 8.

In view of the foregoing, the present disclosure, through one or more of its various aspects, embodiments and/or specific features or sub-components, is thus intended to bring out one or more of the advantages as specifically noted below. While the present disclosure includes description with respect to a medical procedure, the present invention may be used in a variety of other, non-medical, environments.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An electronic forceps system comprising:
a handle comprising a pair of arms distally extending from a hinge at a proximal end of the handle, the pair of arms configured to pivot towards and away from each other at the hinge, the hinge configured to prevent torqueing of the handle and maintain tip alignment and comprising a metal frame having a tweezer shape with an overmolded sheath covering the metal frame, at least one arm of the pair of arms having an electrically-conductive arm element connectable to a power source, wherein:
each arm of the pair of arms includes an arm interface defining a socket;
the electrically-conductive arm element includes a wire connection within the socket; and
the electrically-conductive arm element extends to at least one arm interface of the pair of arm interfaces; and a pair of tips, at least one tip of the pair of tips having an electrically-conductive tip element, wherein:
each tip of the pair of tips comprises a distal working surface;
each tip of the pair of tips comprises a tip interface at a proximal end of each tip, the proximal end of each tip at an opposite end of each tip from the distal working surface, the tip interface configured to fit into the socket of the arm interface such that the distal working surface extends beyond the arm interface and the distal working surface of each tip remains axially aligned with each arm, each tip interface also configured to removably connect to a respective arm interface;
the electrically-conductive tip element is configured to removably and electrically connect to the electrically-conductive arm element via a wire connection within the socket that enables an electrical connection between the power source and the electrically-conductive tip element; and
the electrically-conductive tip element is connected to a heater on the distal working surface.

2. The electronic forceps system according to claim 1, wherein the pair of arms further comprises a magnetically-actuated switch configured to activate the heater when the pair of arms moves towards each other, and further configured to deactivate the heater when the pair of arms moves away from each other.

3. The electronic forceps system according to claim 2, wherein the magnetically-actuated switch is a magnetic reed switch.

4. The electronic forceps system according to claim 1, wherein each arm of the pair of arms further comprises a frame completely covered by an electrically and fluidically insulative covering which is more flexible than the frame.

5. The electronic forceps system according to claim 1, wherein each arm of the pair of arms is jogged along the length of thereof.

6. The electronic forceps system according to claim 1, wherein:
each arm of the pair of arms further comprises a frame covered by an electrically and fluidically insulative covering which is more flexible than the frame;
wherein the pair of arms further comprises a magnetically-actuated switch affixed to the frame and configured to activate the heater when the pair of arms moves towards each other, and further configured to deactivate the heater when the pair of arms moves away from each other.

7. The electronic forceps system according to claim 1, wherein each tip interface is configured to removably connect to each respective arm interface by axially inserting one of the tip interface and the arm interface into and along the length of the other of the tip interface and the arm interface, such that each tip is secured to and aligns with a respective arm.

8. The electronic forceps system according to claim 1, wherein:
each tip interface is configured to removably connect to the arm interface by axially inserting the tip interface into and along the length of the arm interface,
each arm interface further comprises a movable lock configured to engage the tip interface such that each tip is secured to and aligns with a respective arm.

9. The electronic forceps system according to claim 8, wherein the movable lock comprises:
a tab end; and a cam end, wherein when the tab end is pushed, the cam end pivots such that a cam surface engages a said tip interface.

10. The electronic forceps system according to claim 9, wherein:
each arm comprises a recess, and upon engagement of the cam surface with the tip interface, the tab end fits in the recess of each respective arm.

11. The electronic forceps system according to claim 8, wherein:
each tip interface is split into two prongs along the length thereof, with a channel between the two prongs, and
each arm further comprises a pin extending orthogonally to the length direction of the tip interface, such that upon the insertion of the tip interface into the arm interface, the pin slides in the channel.

12. The electronic forceps system according to claim 1, wherein the tip interface is configured to removably connect to the arm interface via at least one of press-fit connection, bayonet connection, peg-and-hole connection, screw connection, rotator knob connection, movable lock, and cam locking lever connection.

13. The electronic forceps system according to claim 1, wherein the electrically-conductive arm element is a wire.

14. The electronic forceps system according to claim 1, wherein the electrically-conductive arm element is unitarily formed with a respective said arm.

15. The electronic forceps system according to claim 1, wherein the pair of tips are proximally interconnected such that the pair of tips has a tweezer configuration.

16. The electronic forceps system according to claim 1, wherein:
one of each said tip interface and each said arm interface comprises a tab,
the other of each said tip interface and each said arm interface comprises an attachment slot with an opening configured to receive the tab,
the tab is guidable in the attachment slot along the length direction of a respective said arm to attach the respective said tip to a respective said arm.

17. The electronic forceps system according to claim 16, wherein:
one of each said tip interface and each said arm interface further comprises a guide pin,
the other of each said tip interface and each said arm interface further comprises a guide slot configured to receive the guide,
the guide pin is guidable in the guide slot along the length direction of a respective said arm.

18. The forceps system according to claim 1, further comprising a forceps tip aligner comprising:
an upper half having a pair of upper channels; and
a lower half having a pair of lower channels, wherein the pair of upper and lower channels together are configured to removably accommodate and maintain in alignment a respective said tip of the pair of tips such that the pair of tips are removably sandwiched between the upper half and the lower half.

19. The forceps system according to claim 18, further comprising:
a plurality of pins on one of the upper half and the lower half; and
a plurality of sockets on the other of the upper half and the lower half, wherein the plurality of sockets are configured to removably accommodate a respective pin of the plurality of pins such that the upper half and lower half are aligned with each other.

20. The electronic forceps system of claim 1, wherein each arm interface of the pair of arm interfaces comprises a socket and each tip interface comprises a member that fits into the socket with a press-fit.

21. The electronic forceps system of claim 1, wherein the overmolded sheath is formed of a material having a Shore A durometer rating of at least 90.

22. The electronic forceps system of claim 1, wherein the socket comprises a sensor configured to detect a connection of a tip of the pair of tips into the socket.

23. A forceps handpiece comprising:
a handle comprising a hinge and formed of a metal frame having a tweezer shape with an overmolded sheath covering the metal frame;
a pair of arms distally extending from the handle and configured to pivot towards and away from each other, at least one arm of the pair of arms having an electrically-conductive arm element connectable to a power source, wherein:
each arm of the pair of arms comprises a respective pair of arm interfaces defining a socket; and
the electrically-conductive arm element extends to at least one interface of the pair of arm interfaces, the at least one interface comprising a wire connection within the socket that enables an electrical connection to the power source;
each arm interface of the pair of arm interfaces is configured to mechanically connect to a respective tip interface of a pair of tips via the socket, with the tip interface fitting into the socket such that a working surface of the each arm extends beyond the arm interface; and
at least one arm interface is configured to electrically connect to a heater on a distal working surface of a respective at least one tip of the pair of tips via the arm element.

24. The forceps handpiece according to claim 23, wherein the pair of arms further comprises a magnetically-actuated switch configured to activate the heater when the pair of arms moves towards each other, and further configured to deactivate the heater when the pair of arms moves away from each other.

25. The forceps handpiece according to claim 24, wherein the magnetically-actuated switch is a magnetic reed switch.

26. The forceps handpiece according to claim 23, wherein each arm of the pair of arms further comprises a frame covered by an electrically and fluidically insulative covering which is more flexible than the frame.

27. The forceps handpiece according to claim 23, wherein each arm of the pair of arms is jogged along the length of thereof.

28. The forceps handpiece according to claim 23, wherein:
each arm of the pair of arms further comprises a frame covered by an electrically and fluidically insulative covering which is more flexible than the frame;
wherein the pair of arms further comprises a magnetically-actuated switch affixed to the frame and configured to activate the heater when the pair of arms moves towards each other, and further configured to deactivate the heater when the pair of arms moves away from each other.

29. The forceps handpiece according to claim 23, wherein the arm interface is configured to removably connect to the tip interface by axially inserting one of the tip interface and the arm interface into and along the length of the other of the tip interface and the arm interface, such that each tip is secured to and aligns with a respective arm.

30. The forceps handpiece according to claim 23, wherein the arm interface is configured to removably connect to the tip interface via one of press-fit connection, bayonet connection, peg-and-hole connection, screw connection, rotator knob connection, movable lock, and cam locking lever connection.

31. The forceps handpiece according to claim 23, further comprising a forceps tip aligner comprising:
an upper half having a pair of upper channels; and
a lower half having a pair of lower channels, wherein the pair of upper and lower channels together are configured to removably accommodate and maintain in alignment a respective said tip of the pair of tips such that the pair of tips are removably sandwiched between the upper half and the lower half.

32. The forceps handpiece according to claim 31, further comprising:
a plurality of pins on one of the upper half and the lower half; and
a plurality of sockets on the other of the upper half and the lower half, wherein the plurality of sockets are configured to removably accommodate a respective pin of the plurality of pins such that the upper half and lower half are aligned with each other.

33. A forceps tip system comprising:
a pair of tips;
a pair of tip interfaces respectively located at a proximal end of the pair of tips, the pair of tip interfaces configured to removably connect to a socket of a respective pair of arm interfaces of a respective pair of arms of a forceps handle with a press-fit that maintains the pair of tip interfaces in the socket, at least one tip interface of the pair of tip interfaces including a wire connection within the socket that enables an electrical connection between a respective tip of the pair of tips and a respective arm of the pair of arms;
a pair of working surfaces located on respective distal ends of the pair of tips, the distal ends of the pair of tips positioned at an opposite end of the pair of tips from the pair of tip interfaces;
an electrically-conductive tip element located on at least one tip of the pair of tips and configured to electrically connect to a respective at least one arm interface of the pair of arm interfaces; and
a heater located on the at least one working surface of the pair of working surfaces and electrically connected to the electrically-conductive tip element.

34. The forceps tip system according to claim 33, wherein the pair of tip interfaces is configured to removably connect to the respective pair of arm interfaces by axially inserting one of the pair of tip interfaces and the pair arm interfaces into and along the length of the other of the pair of tip interfaces and the pair of arm interfaces, such that the pair of tips is respectively secured to and aligns with the pair of arms.

35. The forceps tip system according to claim 33, wherein the pair of tip interfaces is configured to removably connect to the pair arm interfaces via one press-fit connection, bayonet connection, peg-and-hole connection, screw connection, rotator knob connection, movable lock, and cam locking lever connection.

36. The forceps tip system according to claim 33, further comprising:
another electrically-conductive tip element located on a second tip of the pair of tips and configured to electrically connect to a respective second arm interface of the pair of arm interfaces; and
another heater located on a second working surface of the pair of working surfaces and electrically connected to the another electrically-conductive tip element.

37. The forceps tip system according to claim 33, further comprising a forceps tip aligner comprising:
an upper half having a pair of upper channels; and
a lower half having a pair of lower channels, wherein the pair of upper and lower channels together are configured to removably accommodate and maintain in alignment a respective said tip of the pair of tips such that the pair of tips are removably sandwiched between the upper half and the lower half.

38. The forceps tip system according to claim 37, further comprising:
a plurality of pins on one of the upper half and the lower half; and
a plurality of sockets on the other of the upper half and the lower half, wherein the plurality of sockets are configured to removably accommodate a respective pin of the plurality of pins such that the upper half and lower half are aligned with each other.

* * * * *